(12) United States Patent
Honma et al.

(10) Patent No.: US 8,536,359 B2
(45) Date of Patent: Sep. 17, 2013

(54) ALKOXYSILANE COMPOUNDS HAVING FLUOROALKYL GROUP AND METHOD OF PREPARING THE SAME

(75) Inventors: Takayuki Honma, Joetsu (JP); Ayumu Kiyomori, Joetsu (JP); Tohru Kubota, Joetsu (JP); Daijitsu Harada, Joetsu (JP); Hiroyuki Yamazaki, Joetsu (JP); Masaki Takeuchi, Joetsu (JP)

(73) Assignee: Shin-Etsu Chemical Co., Ltd., Tokyo (JP)

( * ) Notice: Subject to any disclaimer, the term of this patent is extended or adjusted under 35 U.S.C. 154(b) by 0 days.

(21) Appl. No.: 13/444,254

(22) Filed: Apr. 11, 2012

(65) Prior Publication Data

US 2012/0264964 A1    Oct. 18, 2012

(30) Foreign Application Priority Data

Apr. 12, 2011    (JP) .................. 2011-087866

(51) Int. Cl.
*C07F 7/02*    (2006.01)
(52) U.S. Cl.
USPC ............................................................ 556/400
(58) Field of Classification Search
USPC ............................................................ 556/400
See application file for complete search history.

(56) References Cited

FOREIGN PATENT DOCUMENTS

| | | |
|---|---|---|
| JP | 63-250389 A | 10/1988 |
| JP | 2008-297400 A | 12/2008 |

OTHER PUBLICATIONS

"3.5 Application as Functional Surface Treatment Agent"; Silicon Handbook, edited by Itoh Kunio, Kikkan kogyo Shimbun, Ltd., p. 79, Line 9 to p. 80, Line 5, Published on Aug. 31, 1990.(w/partial English translation).

*Primary Examiner* — Johann R Richter
*Assistant Examiner* — Kofi Adzamli
(74) *Attorney, Agent, or Firm* — Westerman, Hattori, Daniels & Adrian, LLP

(57) ABSTRACT

Disclosed are alkoxysilane compounds having two fluoroalkyl groups and represented by the following general formula (1):

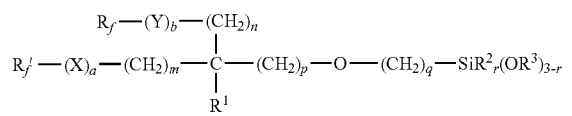

(1)

wherein $R_f$ and $R_f^1$ are each a fluoroalkyl group of 1 to 10 carbon atoms, $R^1$ is a hydrogen atom or an aliphatic monovalent hydrocarbon group of 1 to 6 carbon atoms, $R^2$ and $R^3$ are each methyl group or ethyl group, X and Y are each an ether linkage or an ester linkage, a and b are each 0 or 1, m, n and p are each an integer of 0 to 6, q is an integer of 1 to 6, and r is an integer of 0 to 2. By treating an inorganic material with the alkoxysilane compound having ether linkage and two fluoroalkyl groups, high water and oil repellency and high sliding properties can be imparted to the inorganic material. The alkoxysilane compounds can be easily purified, owing to enhancement of volatility by the branched structure.

4 Claims, 7 Drawing Sheets

ALKOXYSILANE COMPOUNDS HAVING FLUOROALKYL GROUP AND METHOD OF PREPARING THE SAME

CROSS-REFERENCE TO RELATED APPLICATION

This non-provisional application claims priority under 35 U.S.C. §119(a) on Patent Application No. 2011-087866 filed in Japan on Apr. 12, 2011, the entire contents of which are hereby incorporated by reference.

TECHNICAL FIELD

The present invention relates to alkoxysilane compounds having ether linkage and two fluoroalkyl groups which are useful as a surface treating agent, a coating additive, and a polymer modifier, and a method of preparing the alkoxysilane compounds.

BACKGROUND ART

Hitherto, such organic silicon compounds as alkylalkoxysilane compounds and fluoroalkylalkoxysilane compounds have been known to be useful as surface treating agents, fiber treating agents, and coating additives. Especially, it has been known that when a fluoroalkylalkoxysilane compound is used to treat a surface of an inorganic material (for example, glass, metal, or oxide) for the purpose of controlling water repellency, oil repellency or sliding properties (slidability of droplets) of the surface, covalent bonds formed between the alkoxysilane compound and the surface hydroxyl group of the inorganic material enable strong bonding between the fluoroalkylalkoxysilane compound and the inorganic material, whereby the weather resistance and retention of the modified surface properties are improved (see Non-Patent Document 1: "Silicone Handbook," Edited by Itoh Kunio, Nikkan Kogyo Shimbun, Ltd., p. 79, line 9 to p. 80, line 5).

Where a fluoroalkylalkoxysilane compound is used for surface treatment, the compound is very effective in improving the static contact angle representing water repellency and oil repellency. In this case, however, the angle at which a droplet starts sliding along the surface treated (sliding angle) as well as the hysteresis ($\theta_A - \theta_R$) obtained from the advancing contact angle ($\theta_A$) and receding contact angle ($\theta_R$) are high; in other words, the dynamic contact angle is insufficient. The dynamic behavior is particularly important as an index to sliding properties (droplet removal performance), and an improvement thereof is being requested.

For enhancing lubricity, there have been developed alkoxysilane compounds having a perfluoropolyether group (see Patent Document 1: JP-A S63-250389). The alkoxysilane compounds, however, have been unsatisfactory in balance between the water and oil repellency and the sliding properties.

For realizing high water repellency and oil repellency by use of a short fluoroalkyl chain, there have been developed fluorine-containing acrylate compounds having two fluoroalkyl chains (see Patent Document 2: JP-A 2008-297400). Although these acrylate compounds have polymerizing properties, they lack reactivity with inorganic materials and, hence, they cannot impart water repellency, oil repellency and sliding properties to inorganic materials such as glasses, silicon wafers and fillers.

CITATION LIST

Patent Document 1: JP-A S63-250389
Patent Document 2: JP-A 2008-297400
Non-Patent Document 1: "Silicone Handbook," edited by Itoh Kunio, Nikkan Kogyo Shimbun, Ltd., p. 79, line 9, to p. 80, line 5.

SUMMARY OF THE INVENTION

The present invention has been made in consideration of the above-mentioned circumstance. Accordingly, it is an object of the present invention to provide an alkoxysilane compound having two fluoroalkyl groups which has an ether linkage and two fluoroalkyl chains, can impart higher water and oil repellency and higher sliding properties to inorganic materials owing to the alkoxysilyl group and can be easily purified due to enhancement of volatility by a branched structure, and a method of preparing the alkoxysilane compound.

In order to attain the above object and obtain a silane compound capable of imparting higher water and oil repellency and higher sliding properties to inorganic materials by use of a short fluoroalkyl chain, the present inventors made extensive and intensive investigations, and, as a result, they found the following. Alkoxysilane compounds having two fluoroalkyl groups and represented by the following general formula (1):

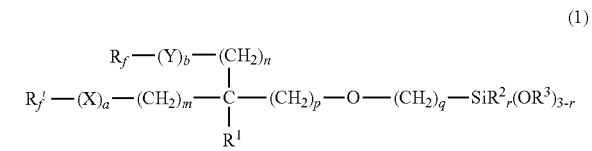

(wherein $R_f$ and $R_f'$ are each independently a fluoroalkyl group of 1 to 10 carbon atoms, $R^1$ is a hydrogen atom or an aliphatic monovalent hydrocarbon group of 1 to 6 carbon atoms, $R^2$ and $R^3$ are each independently methyl group or ethyl group, X and Y are each independently an ether linkage or an ester linkage, a and b are each 0 or 1, m, n and p are each an integer of 0 to 6, q is an integer of 1 to 6, and r is an integer of 0 to 2) were found to be capable of imparting high water and oil repellency and high sliding properties to inorganic materials, owing to the presence of the ether linkage and two short fluoroalkyl chains. In addition, the alkoxysilane compounds were found to be capable of being easily purified owing to enhancement of volatility by the branched structure. Based on the findings, the present invention has been completed.

According to the present invention, there are provided alkoxysilane compounds having fluoroalkyl groups and a method of preparing the alkoxysilane compounds, as follows.

[1] An alkoxysilane compound having two fluoroalkyl groups and represented by the following general formula (1):

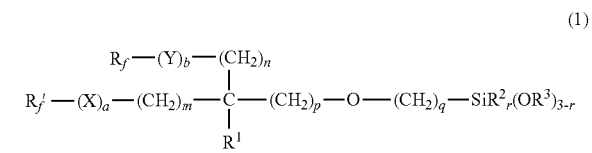

wherein $R_f$ and $R_f'$ are each independently a fluoroalkyl group of 1 to 10 carbon atoms, $R^1$ is a hydrogen atom or an aliphatic monovalent hydrocarbon group of 1 to 6 carbon atoms, $R^2$ and $R^3$ are each independently methyl group or ethyl group, X and Y are each independently an ether linkage or an ester linkage, a and b are each 0 or 1, m, n and p are each an integer of 0 to 6, q is an integer of 1 to 6, and r is an integer of 0 to 2.

[2] The alkoxysilane compound having two fluoroalkyl groups according to the above paragraph [1] which is represented by the following general formula (2):

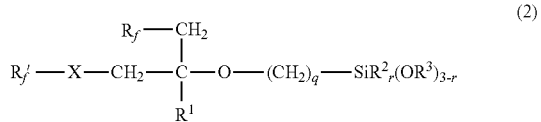

(2)

wherein $R_f$ and $R_f'$ are each independently a fluoroalkyl group of 1 to 10 carbon atoms, $R^1$ is a hydrogen atom or an aliphatic monovalent hydrocarbon group of 1 to 6 carbon atoms, $R^2$ and $R^3$ are each independently methyl group or ethyl group, X is an ether linkage or an ester linkage, q is an integer of 1 to 6, and r is an integer of 0 to 2.

The paragraph [2] is the case where a=1, b=0, m=1, n=1, and p=0 in the formula (1) of the paragraph [1], respectively.

[3] The alkoxysilane compound having two fluoroalkyl groups according to the above paragraph [1] which is represented by the following general formula (3):

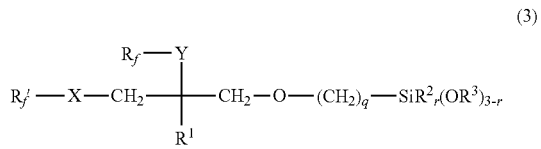

(3)

wherein $R_f$ and $R_f'$ are each independently a fluoroalkyl group of 1 to 10 carbon atoms, $R^1$ is a hydrogen atom or an aliphatic monovalent hydrocarbon group of 1 to 6 carbon atoms, $R^2$ and $R^3$ are each independently methyl group or ethyl group, X and Y are each independently an ether linkage or an ester linkage, q is an integer of 1 to 6, and r is an integer of 0 to 2.

The paragraph [3] is the case where a=1, b=1, m=1, n=1, n=0, and p=1 in the formula (1) of the paragraph [1], respectively.

[4] The alkoxysilane compound having two fluoroalkyl groups according to the above paragraph [1] which is represented by the following formula (4):

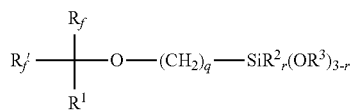

(4)

wherein $R_f$ and $R_f'$ are each independently a fluoroalkyl group of 1 to 10 carbon atoms, $R^1$ is a hydrogen atom or an aliphatic monovalent hydrocarbon group of 1 to 6 carbon atoms, $R^2$ and $R^3$ are each independently methyl group or ethyl group, q is an integer of 1 to 6, and r is an integer of 0 to 2.

The paragraph [4] is the case where a=0, b=0, m=0, n=0, and p=0 in the formula (1) of the paragraph [1], respectively.

[5] A method of preparing the alkoxysilane compound having two fluoroalkyl groups according to any one of the above paragraphs [1] to [4], including reacting an olefin having two fluoroalkyl groups represented by the following general formula (5):

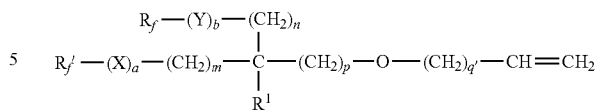

(5)

wherein $R_f$ and $R_f'$ are each independently a fluoroalkyl group of 1 to 10 carbon atoms, $R^1$ is a hydrogen atom or an aliphatic monovalent hydrocarbon group of 1 to 6 carbon atoms, X and Y are each independently an ether linkage or an ester linkage, a and b are each 0 or 1, m is an integer of 0 to 6, n is an integer of 0 to 6, p is an integer of 0 to 6, and q' is an integer of 0 to 4 with an alkoxysilane hydride compound represented by the following general formula (6):

$$HSiR^2_r(OR^3)_{3-r} \qquad (6)$$

wherein $R^2$ and $R^3$ are each independently methyl group or ethyl group, and r is an integer of 0 to 2.

[6] A method of preparing the alkoxysilane compound having two fluoroalkyl groups according to any one of the above paragraphs [1] to [4], including reacting a chlorosilane compound having two fluoroalkyl groups represented by the following general formula (7):

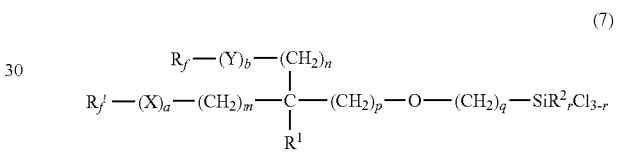

(7)

wherein $R_f$ and $R_f'$ are each independently a fluoroalkyl group of 1 to 10 carbon atoms, $R^1$ is a hydrogen atom or an aliphatic monovalent hydrocarbon group of 1 to 6 carbon atoms, $R^2$ is methyl group or ethyl group, X and Y are each independently an ether linkage or an ester linkage, a is 0 or 1, b is 0 or 1, m, n and p are each an integer of 0 to 6, q is an integer of 1 to 6, and r is an integer of 0 to 2 with a compound represented by the following general formula (8):

$$R^3OH \qquad (8)$$

wherein $R^3$ is methyl group or ethyl group.

Advantageous Effects of the Invention

According to the present invention, by using the above-mentioned alkoxysilane compound having ether linkage and two fluoroalkyl groups to treat an inorganic material, it is possible to impart high water and oil repellency and high sliding properties to the inorganic material. Besides, the alkoxysilane compounds according to the present invention can be easily purified due to enhancement of volatility by the branched structure.

DESCRIPTION OF THE PREFERRED EMBODIMENTS

Figure 1:
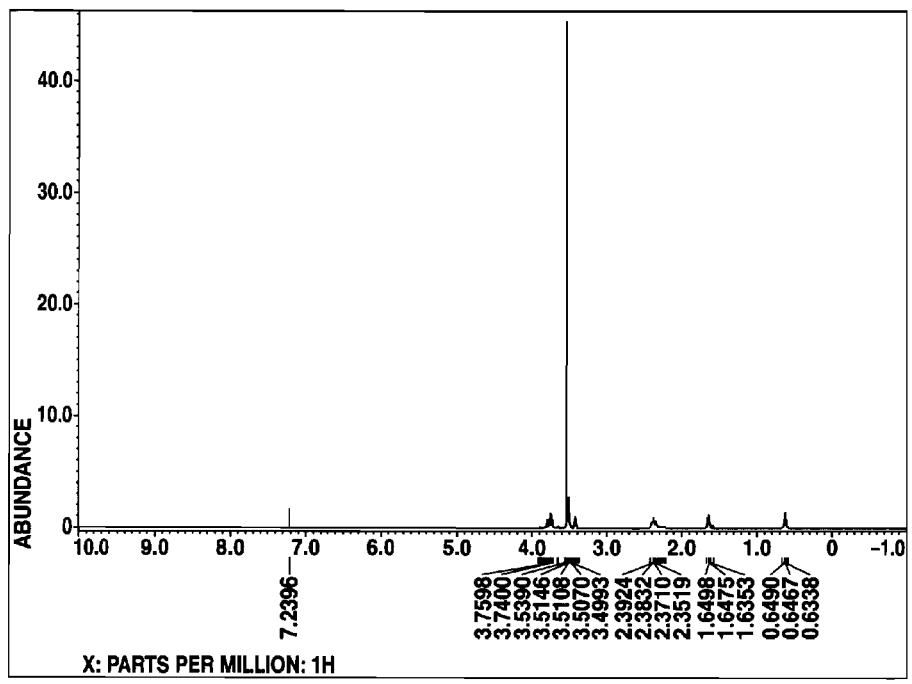
FIG. 1 shows $^1$H-NMR spectrum of an alkoxysilane compound obtained in Example 1.

The alkoxysilane compound having two fluoroalkyl groups according to the present invention is represented by the following general formula (1):

$$R_f'-(X)_a-(CH_2)_m-\underset{\underset{R^1}{|}}{\overset{\overset{R_f-(Y)_b-(CH_2)_n}{|}}{C}}-(CH_2)_p-O-(CH_2)_q-SiR^2_r(OR^3)_{3-r} \quad (1)$$

wherein $R_f$ and $R_f'$ are each a fluoroalkyl group of 1 to 10 carbon atoms, which may respectively be identical or different, $R^1$ is a hydrogen atom or an aliphatic monovalent hydrocarbon group of 1 to 6 carbon atoms, $R^2$ and $R^3$ are each methyl group or ethyl group, which may respectively be identical or different, X and Y are each an ether linkage or an ester linkage which may respectively be identical or different, a and b are each 0 or 1, m, n and p are each an integer of 0 to 6, q is an integer of 1 to 6, and r is an integer of 0 to 2.

In the general formula (1), $R_f$ and $R_f'$ are each a fluoroalkyl group of 1 to 10 carbon atoms, which may respectively be identical or different. Specific examples of the fluoroalkyl groups include straight chain fluoroalkyl groups such as trifluoromethyl, pentafluoroethyl, nonafluorobutyl, tridecafluorohexyl, hexadecafluorooctyl, 2,2,2-trifluroethyl, 3,3,3,2,2-pentafluoropropyl, 5,5,5,4,4,3,3,2,2-nonafluoropentyl, 7,7,7,6,6,5,5,4,4,3,3,2,2-tridecafluoroheptyl, 9,9,9,8,8,7,7,6,6,5,5,4,4,3,3,2,2-hexadecafluorononyl, 3,3,3-trifluropropyl, 4,4,4,3,3-pentafluorobutyl, 6,6,6,5,5,4,4,3,3-nonafluorohexyl, 8,8,8,7,7,6,6,5,5,4,4,3,3-tridecafluorooctyl, 10,10,10,9,9,8,8,7,7,6,6,5,5,4,4,3,3-hexadecafluorodecyl, 4,4,4-trifluorobutyl, 5,5,5,4,4-pentafluoropentyl, 7,7,7,6,6,5,5,4,4-nonafluoroheptyl, 9,9,9,8,8,7,7,6,6,5,5,4,4-tridecafluorononyl, 5,5,5-trifluoropentyl, 6,6,6,5,5-pentafluorohexyl, 8,8,8,7,7,6,6,5,5-nonafluorooctyl, 10,10,10,9,9,8,8,7,7,6,6,5,5-tridecafluorodecyl, 6,6,6-triflurohexyl, 7,7,7,6,6-pentafluoroheptyl, 9,9,9,8,8,7,7,6,6-nonafluorononyl, 7,7,7-trifluoroheptyl, 8,8,8,7,7-pentafluorooctyl, 10,10,10,9,9,8,8,7,7-nonafluorodecyl, 9,9,9-trifluorononyl, and 10,10,10,9,9-pentafluorodecyl, and branched fluoroalkyl groups such as 1,1,1,3,3,3-hexafluoroisopropyl, and 2,2-bis(trifluoromethyl)propyl.

In the general formula (1), $R^1$ is a hydrogen atom or an aliphatic monovalent hydrocarbon group of 1 to 6 carbon atoms. The aliphatic monovalent hydrocarbon group of 1 to 6 carbon atoms may be a straight chain, branched or cyclic alkyl group or alkenyl group. Specific examples of the aliphatic monovalent hydrocarbon group of 1 to 6 carbon atoms include methyl, ethyl, propyl, isopropyl, butyl, isobutyl, tert-butyl, pentyl, cyclopentyl, hexyl, cyclohexyl, vinyl, allyl, methallyl, and butenyl groups. Preferred examples of $R^1$ are hydrogen atom and methyl group.

In the general formula (1), $R^2$ and $R^3$ are identical or different and each methyl group or ethyl group.

The capitals X and Y are each independently an ether linkage or an ester linkage.

The letters m, n and p are each an integer of 0 to 6, q is an integer of 1 to 6, and r is an integer of 0 to 2. Preferably, m, n and p are each 0 or 1, q is an integer of 1 to 3, and r is 1 or 2.

Specific examples of the compounds represented by the general formula (1) according to the present invention include compounds represented by the following general formula (2) such as Compounds A and B, compounds represented by the following general formula (3) such as Compounds C to E, and compounds represented by the following general formula (4) such as Compound F, but these examples are not restrictive of the present invention:

$$R_f'-X-CH_2-\underset{\underset{R^1}{|}}{\overset{\overset{R_f-CH_2}{|}}{C}}-O-(CH_2)_q-SiR^2_r(OR^3)_{3-r} \quad (2)$$

wherein $R_f$ and $R_f'$ are identical or different and each a fluoroalkyl group of 1 to 10 carbon atoms, $R^1$ is a hydrogen atom or an aliphatic monovalent hydrocarbon group of 1 to 6 carbon atoms, $R^2$ and $R^3$ are identical or different and each methyl group or ethyl group, X is an ether linkage or an ester linkage, q is an integer of 1 to 6, and r is an integer of 0 to 2;

Compound A:

$$R_f^\alpha\diagdown O\diagup\overset{R_f^\beta}{\underset{}{\diagdown}}\diagdown O\diagdown R^\gamma$$

Compound B:

$$R_f^\alpha-\underset{\underset{O}{\|}}{C}-O\diagup\overset{R_f^\beta}{\underset{}{\diagdown}}\diagdown O\diagdown R^\gamma$$

$$R_f'-X-CH_2-\underset{\underset{R^1}{|}}{\overset{\overset{R_f-Y}{|}}{\diagup\!\diagdown}}-CH_2-O-(CH_2)_q-SiR^2_r(OR^3)_{3-r} \quad (3)$$

wherein $R_f$ and $R_f'$ are identical or different and each a fluoroalkyl group of 1 to 10 carbon atoms, $R^1$ is a hydrogen atom or an aliphatic monovalent hydrocarbon group of 1 to 6 carbon atoms, $R^2$ and $R^3$ are identical or different and each methyl group or ethyl group, X and Y are identical or different and each an ether linkage or an ester linkage, q is an integer of 1 to 6, and r is an integer of 0 to 2;

Compound C:

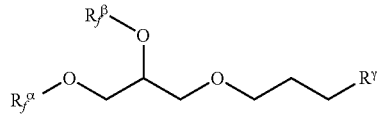

Compound D:

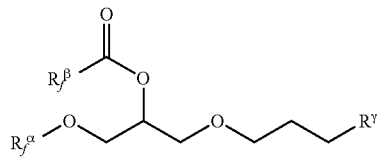

Compound E:

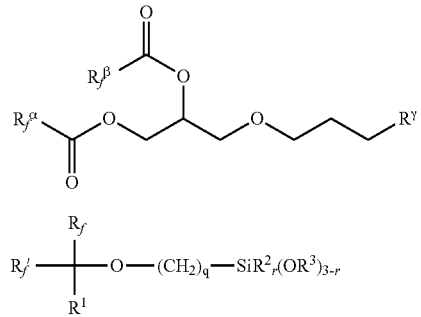

$$R_f' \overset{R_f}{\underset{R^1}{\vphantom{|}}} O-(CH_2)_q-SiR^2_r(OR^3)_{3-r} \quad (4)$$

wherein $R_f$ and $R_f'$ are identical or different and each a fluoroalkyl group of 1 to 10 carbon atoms, $R^1$ is a hydrogen atom or an aliphatic monovalent hydrocarbon group of 1 to 6 carbon atoms, $R^2$ and $R^3$ are identical or different and each methyl group or ethyl group, q is an integer of 1 to 6, and r is an integer of 0 to 2.

Compound F:

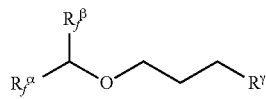

Here, examples of $R_f^\alpha$, $R_f^\beta$ and $R^\gamma$ in the compounds A to F include the groups as set forth in the following Tables 1 and 2, and $R_f^\alpha$ and $R_f^\beta$ may be identical or different.

TABLE 1

| Examples of $Rf^\alpha$ and $Rf^\beta$ in Compounds A to F |
|---|
| —$CF_3$ |
| —$(CF_2)_2F$ |
| —$(CF_2)_4F$ |
| —$(CF_2)_6F$ |
| —$(CF_2)_8F$ |
| —$CH_2CF_3$ |
| —$CH_2(CF_2)_2F$ |
| —$CH_2(CF_2)_4F$ |
| —$CH_2(CF_2)_6F$ |
| —$CH_2(CF_2)_8F$ |
| —$(CH_2)_2CF_3$ |

TABLE 1-continued

| Examples of $Rf^\alpha$ and $Rf^\beta$ in Compounds A to F |
|---|
| —$(CH_2)_2(CF_2)_2F$ |
| —$(CH_2)_2(CF_2)_4F$ |
| —$(CH_2)_2(CF_2)_6F$ |
| —$(CH_2)_2(CF_2)_8F$ |
| —$(CH_2)_3CF_3$ |
| —$(CH_2)_3(CF_2)_2F$ |
| —$(CH_2)_3(CF_2)_4F$ |
| —$(CH_2)_3(CF_2)_6F$ |
| —$(CH_2)_4CF_3$ |
| —$(CH_2)_4(CF_2)_2F$ |
| —$(CH_2)_4(CF_2)_4F$ |
| —$(CH_2)_4(CF_2)_6F$ |
| —$(CH_2)_5CF_3$ |
| —$(CH_2)_5(CF_2)_2F$ |
| —$(CH_2)_5(CF_2)_4F$ |
| —$(CH_2)_6CF_3$ |
| —$(CH_2)_6(CF_2)_2F$ |
| —$(CH_2)_6(CF_2)_4F$ |
| —$(CH_2)_8CF_3$ |
| —$(CH_2)_8(CF_2)_2F$ |
| —$CH(CF_3)_2$ |
| —$CH_2C(CH_3)(CF_3)_2$ |

TABLE 2

| Examples of $R^\gamma$ in Compounds A to F |
|---|
| —$Si(OCH_3)_3$ |
| —$Si(CH_3)(OCH_3)_2$ |
| —$Si(CH_3)_2(OCH_3)$ |
| —$Si(OC_2H_5)_3$ |
| —$Si(CH_3)(OC_2H_5)_2$ |
| —$Si(CH_3)_2(OC_2H_5)$ |

The alkoxysilane compound having two fluoroalkyl groups represented by the above general formula (1) may be prepared, for example, by reacting an olefin having two fluoroalkyl groups represented by the following general formula (5):

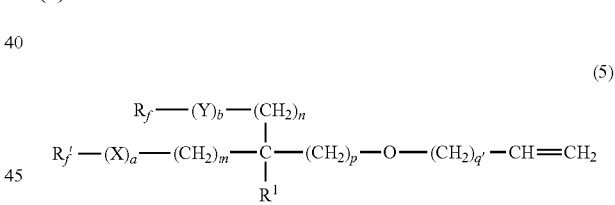

(5)

wherein $R_f$ and $R_f'$ are identical or different and each a fluoroalkyl group of 1 to 10 carbon atoms, $R^1$ is a hydrogen atom or an aliphatic monovalent hydrocarbon group of 1 to 6 carbon atoms, X and Y are identical or different and each an ether linkage or an ester linkage, a and b are each 0 or 1, m is an integer of 0 to 6, n is an integer of 0 to 6, p is an integer of 0 to 6, and q' is an integer of 0 to 4 with an alkoxysilane hydride compound represented by the following general formula (6):

$$HSiR^2_r(OR^3)_{3-r} \quad (6)$$

wherein $R^2$ and $R^3$ are each independently methyl group or ethyl group, and r is an integer of 0 to 2. The reaction is preferably carried out in the presence of a transition metal catalyst, which is preferably a platinum catalyst.

In the general formulas (5) and (6), $R_f$, $R_f'$, $R^1$, $R^2$, $R^3$, X, Y, m, n, p, r, a and b are the same as defined in the general formula (1), and q' is an integer of 0 to 4, preferably 1.

Specific examples of the compound represented by the general formula (5) include the following Compounds a to f, but these examples are not restrictive of the present invention.

Compound a:

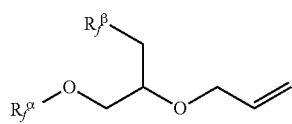

Compound b:

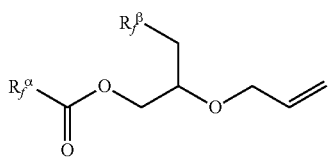

Compound c:

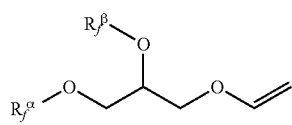

Compound d:

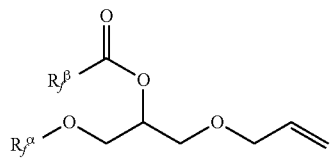

Compound e:

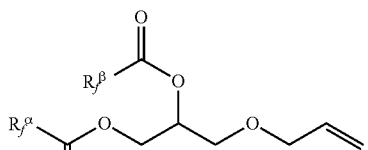

Compound f:

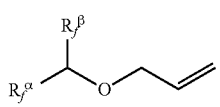

It is to be noted that examples of $R_f^\alpha$ and $R_f^\beta$ in the compounds a to f include the groups as set forth in the above Table 1, and $R_f^\alpha$ and $R_f^\beta$ may be identical or different.

Specific examples of the alkoxysilane hydride compound of the general formula (6) used in the above reaction include trimethoxysilane, methyldimethoxysilane, dimethylmethoxysilane, triethoxysilane, methyldiethoxysilane, and dimethylethoxysilane.

The ratio between the amounts of the compound of the general formula (5) and the alkoxysilane hydride compound of the general formula (5) is not particularly limited. From the viewpoint of reactivity and productivity, however, the amount of the alkoxysilane hydride compound of the general formula (6) is preferably in the range of 0.5 to 2 mol, particularly 0.7 to 1.2 mol, per 1 mol of the compound of the general formula (5).

Examples of the platinum catalyst to be used in the reaction include chloroplatinic acid, alcohol solutions of chloroplatinic acid, toluene or xylene solution of platinum-1,3-divinyl-1,1,3,3-tetramethyldisiloxane complex, tetrakistriphenylphosphine platinum, dichlorobistriphenylphosphine platinum, dichlorobisacetonitrile platinum, dichlorobisbenzonitrile platinum, and dichlorocyclooctadiene platinum.

The amount of the platinum catalyst to be used is not particularly limited. From the viewpoint of reactivity and productivity, however, the amount of the platinum catalyst is preferably in the range of 0.000001 to 0.01 mol, particularly 0.00001 to 0.001 mol, per 1 mol of the compound represented by the general formula (5).

The reaction temperature of the above reaction is not particularly limited, although the reaction temperature is preferably 0 to 120° C., more preferably 20 to 100° C. The reaction time is preferably 1 to 20 hours, more preferably 1 to 10 hours.

While the above-mentioned reaction proceeds in a solventless condition, a solvent may be used in the reaction. Examples of the solvent which can be used include hydrocarbon solvents such as pentane, hexane, cyclohexane, heptane, isooctane, benzene, toluene, and xylene; ether solvents such as diethyl ether, tetrahydrofuran, and dioxane; ester solvents such as ethyl acetate, and butyl acetate; aprotic polar solvents such as acetonitrile, and N,N-dimethylformamide; and chlorinated hydrocarbon solvents such as dichloromethane, and chloroform. These solvents may be used either singly or as a mixture of two or more of them.

Incidentally, the compounds a to f can be prepared, for example, by the commonly known methods as represented by the following formulas:

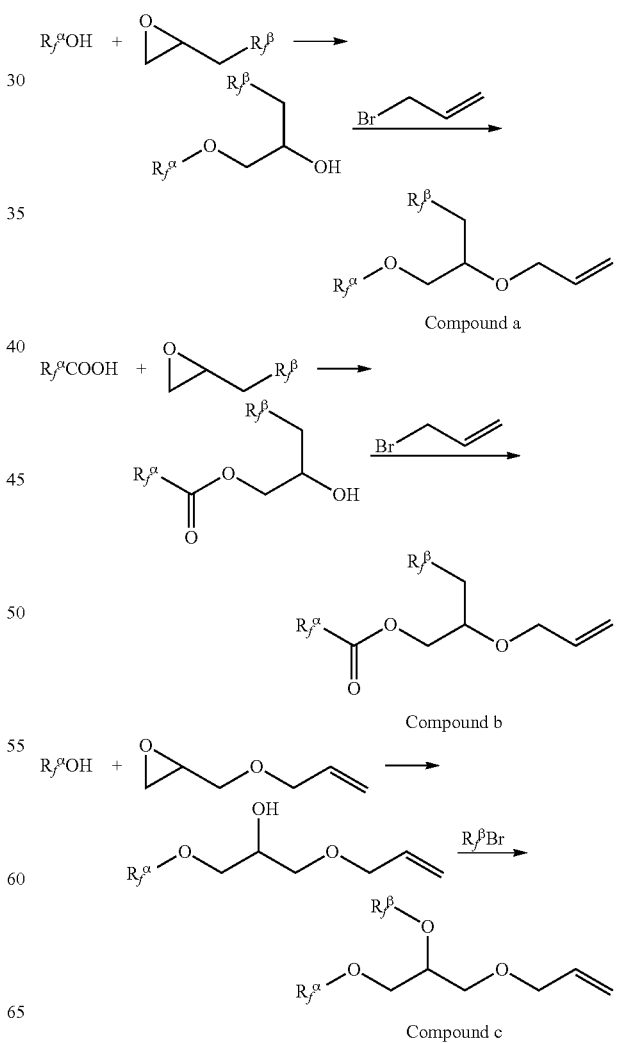

-continued

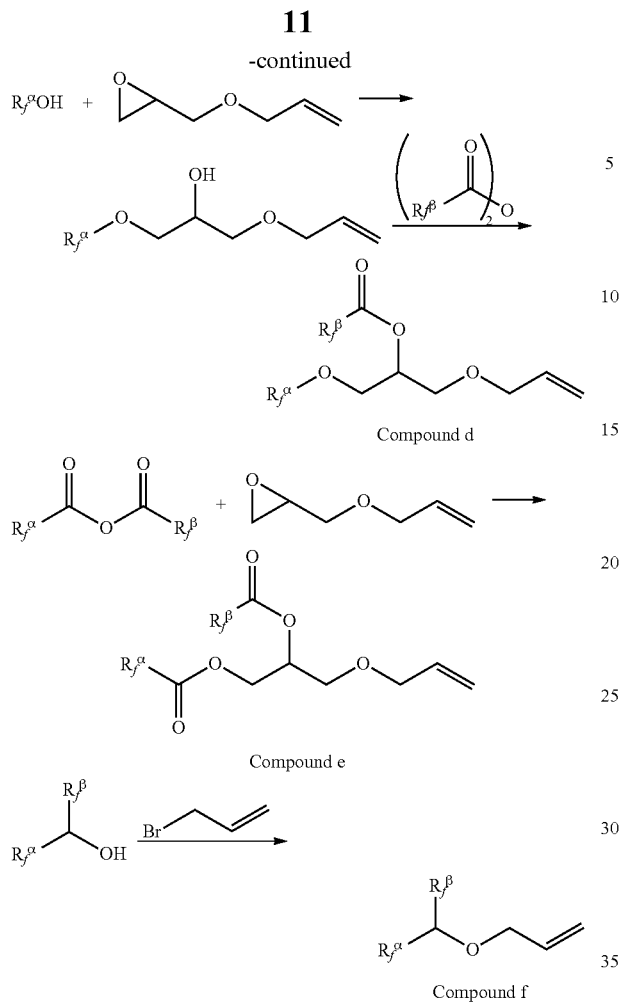

Compound d

Compound e

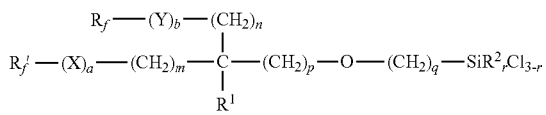

Compound f

In addition, the compound having two fluoroalkyl groups represented by the general formula (1) may be prepared, for example, by reacting a chlorosilane compound having two fluoroalkyl groups represented by the following general formula (7):

(7)

wherein $R_f$ and $R_f'$ are identical or different and each a fluoroalkyl group of 1 to 10 carbon atoms, $R^1$ is a hydrogen atom or an aliphatic monovalent hydrocarbon group of 1 to 6 carbon atoms, $R^2$ is methyl group or ethyl group, X and Y are identical or different and each an ether linkage or an ester linkage, a is 0 or 1, b is 0 or 1, m, n and p are each an integer of 0 to 6, q is an integer of 1 to 6, and r is an integer of 0 to 2 with a compound represented by the following general formula (8):

$$R^3OH \qquad (8)$$

wherein $R^3$ is methyl group or ethyl group.

The letters $R_f$, $R_f'$, $R^1$, $R^2$, $R^3$, X, Y, m, n, p, q, r, a and b in the general formulas (7) and (8) are the same as defined in the above general formula (1).

Specific examples of the compound represented by the above general formula (7) include the following compounds I to VI, which are not restrictive of the present invention.

Compound I:

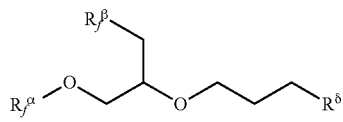

Compound II:

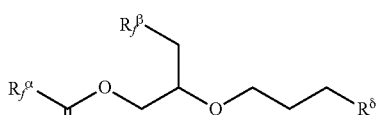

Compound III:

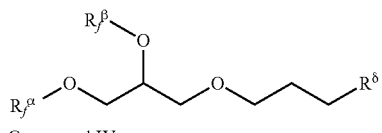

Compound IV:

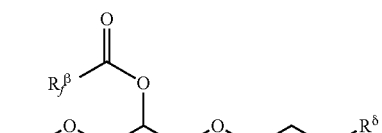

Compound V:

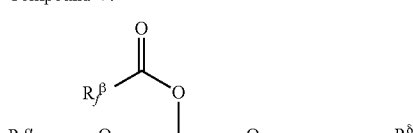

Compound VI:

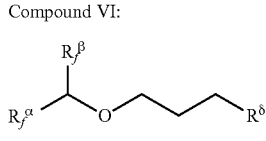

Here, examples of $R_f^\alpha$ and $R_f^\beta$ in the compounds I to VI include the groups as set forth in the above Table 1, and $R_f^\alpha$ and $R_f^\beta$ may be identical or different.

Examples of $R^\delta$ include —SiCl$_3$, —Si(CH$_3$)Cl$_2$, and —Si(CH$_3$)$_2$Cl.

Specific examples of the compound represented by the above general formula (8) include methanol and ethanol.

The ratio between the amount of the compound of the general formula (7) and the amount of the compound of the general formula (8) is not particularly limited. From the viewpoint of reactivity and productivity, however, the amount of the compound of the general formula (8) is preferably in the range of 0.5 to 2.0 mol, particularly 0.7 to 1.2 mol, per 1 mol of the Si—Cl bonds in the compound of the general formula (7).

The above alkoxylation reaction may be carried out in the presence of a basic compound in the reaction system, in order to trap the hydrogen chloride produced during the reaction. Specific examples of the basic compound include amine compounds such as methylamine, dimethylamine, trimethylamine, ethylamine, diethylamine, triethylamine, methyldiisopropylamine, butylamine, dibutylamine, tributylamine, 2-ethylhexylamine, ethylenediamine, pyrrolidine, N-methylpyrrolidine, piperidine, N-methylpiperidine, aniline, n-methylaniline, N,N-dimethylaniline, and toluidine; nitrogen-containing aromatic compounds such as pyridine, quinoline, isoquinoline, picoline, and lutidine; ammonia; and metal alkoxide compounds such as sodium methoxide, and sodium ethoxide.

The amount of the basic compound to be added is preferably in the range of 0.5 to 2.0 mol, particularly 0.7 to 1.2 mol, per 1 mol of the Si—Cl bonds in the compound represented by the general formula (7).

While the above-mentioned reaction proceeds in a solventless condition, a solvent may be used in the reaction. Examples of the solvent which can be used include hydrocarbon solvents such as pentane, hexane, cyclohexane, heptane, isooctane, benzene, toluene, and xylene; ether solvents such as diethyl ether, tetrahydrofuran, and dioxane; ester solvents such as ethyl acetate, and butyl acetate; aprotic polar solvents such as acetonitrile, and N,N-dimethylformamide; and chlorinated hydrocarbon solvents such as dichloromethane, and chloroform. These solvents may be used either singly or as a mixture of two or more of them. The amount of the solvent to be used may be set in an ordinary range of the amount of solvent.

Furthermore, while the conditions for the above reaction are not particularly limited, the reaction temperature may be −20 to 150° C., particularly 0 to 100° C., and the reaction time may be 1 to 20 hours, particularly 2 to 10 hours.

In addition, the compound represented by the general formula (1) can be isolated from the above-mentioned hydrosilylation reaction mixture or alkoxylation reaction mixture by a purification method such as distillation and column separation; especially, isolation by distillation is preferred, since the compound can be obtained thereby in an enhanced purity. The conditions for distillation are not particularly limited, but it is preferable to carry out the distillation at a reduced pressure, for lowering the boiling point of the objective compound.

While the alkoxysilane compounds according to the present invention can be used as they are with no problem, the use of the compounds through dilution with solvent is preferred because of ease of use. Examples of the solvent to be used here include water; alcohol solvents such as methanol, and ethanol; hydrocarbon solvents such as pentane, hexane, cyclohexane, heptane, isooctane, benzene, toluene, and xylene; ketone solvents such as acetone and methyl isobutyl ketone; ether solvents such as diethyl ether, tetrahydrofuran, and dioxane; ester solvents such as ethyl acetate, and butyl acetate; aprotic polar solvents such as acetonitrile, and N,N-dimethylformamide; and chlorinated hydrocarbon solvents such as dichloromethane, and chloroform, of which particularly preferred are water and alcohol solutions. The concentration of the alkoxysilane compound in use through dilution is preferably 0.001 to 50% by weight.

The alkoxysilane compound according to the present invention can be admixed with at least one additive selected from among pigment, anti-foaming agent, lubricant, preservative, pH controlling agent, film forming agent, antistatic agent, anti-fungus agent, surfactant, and dye, within such ranges as not to spoil the advantageous effects of the invention.

The use of the alkoxysilane compounds according to the present invention is not specifically restricted. Examples of the use of the alkoxysilane compounds include an inorganic material surface treating agent, a liquid sealing agent, a casting mold, a resin surface modifier, a polymer modifier, and an aqueous coating additive.

By the use of the alkoxysilane compound according to the present invention, a surface treatment (surface modification) of inorganic materials can be performed. Examples of the inorganic materials include metallic plates, glass plates, metallic fibers, glass fibers, powdery silica, powdery alumina, powdery talc, and powdery calcium carbonate. The material of the glass may be a commonly used type of glass, such as E glass, C glass, and silica glass. Silica glass can be used also as a mold material in nanoimprint technology. The glass fibers are not specifically restricted in product form. There are a diversity of glass fiber products, for example, fiber bundles, twines, and woven fabrics formed from glass filaments having a fiber diameter of 3 to 30 μm.

As the method for treating an inorganic material by the use of the alkoxysilane compound, the conventional methods can be used. The applicable methods include a method in which the inorganic material is immersed in the alkoxysilane compound used as it is or in a diluted state, followed by taking out the inorganic material therefrom and drying it, a method in which the alkoxysilane compound as it is or in a diluted state is sprayed to the surface of the inorganic material, followed by drying the inorganic material, and a method in which the inorganic material is brought into contact with an inert gas accompanied by the alkoxysilane compound.

EXAMPLE

Now, the present invention will be described specifically by showing Examples and Comparative Examples, but the invention is not to be restricted by the following Examples. In the following, Me represents methyl group, and Et represents ethyl group.

Example 1

A flask equipped with a stirrer, a reflux condenser, a dropping funnel and a thermometer was charged with 68 g (0.10 mol) of an olefin represented by the following formula (9),

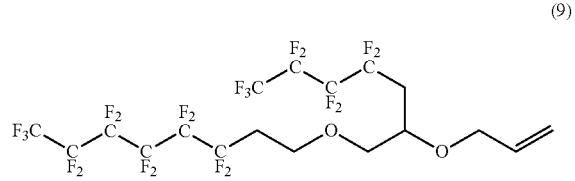 [SMILES: C=CCOC(COCCC(F)(F)C(F)(F)C(F)(F)C(F)(F)C(F)(F)C(F)(F)F)CC(F)(F)C(F)(F)C(F)(F)C(F)(F)F]

(9)

and a toluene solution of a platinum-1,3-divinyl-1,1,3,3-tetramethyldisiloxane complex ($1.0 \times 10^{-4}$ mol based on the olefin), followed by heating to 70° C. After the internal temperature became stable, 9.8 g (0.08 mol) of trimethoxysilane was added dropwise to the flask over four hours at 70 to 80° C., and the reaction mixture was stirred at that temperature for two hours. By distillation of the reaction mixture thus obtained, 52 g of a colorless transparent fraction with a boiling point of 148 to 149° C./0.2 kPa was obtained.

Figure 2:
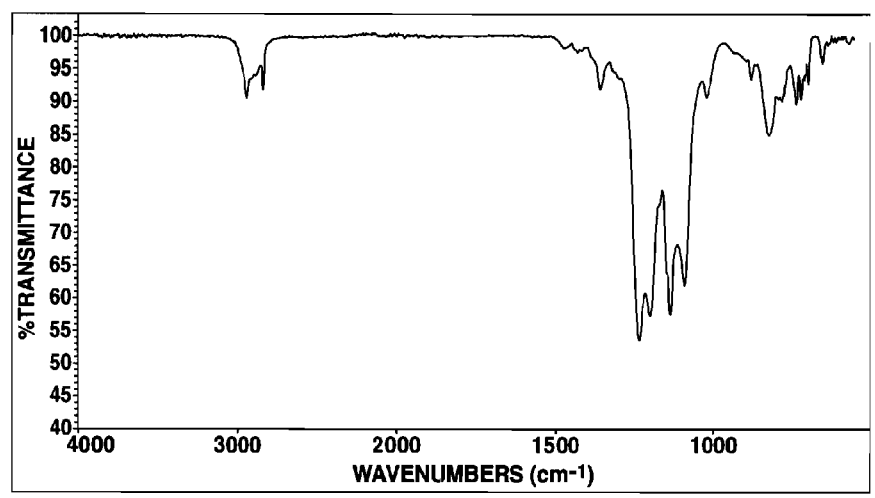
FIG. 2 shows IR spectrum of the alkoxysilane compound obtained in Example 1.

The fraction obtained was subjected to measurement of mass spectrum, $^1$H-NMR spectrum (heavy chloroform solvent), and IR spectrum, by a chemical ionization method using isobutane gas as a reaction gas. The result of mass spectrum is set forth below. FIG. 1 shows a $^1$H-NMR spectrum chart, and FIG. 2 shows an IR spectrum chart.

Mass spectrum: m/z 771, 623, 393, 277, 149, 121

Based on the above results, the compound obtained was identified as a compound of the following formula (10).

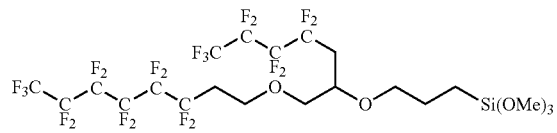

(10)

Example 2

A flask equipped with a stirrer, a reflux condenser, a dropping funnel and a thermometer was charged with 87 g (0.15 mol) of an olefin represented by the following formula (11),

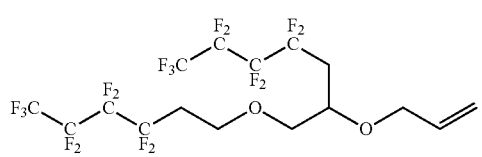

(11)

and a toluene solution of a platinum-1,3-divinyl-1,1,3,3-tetramethyldisiloxane complex ($1.0 \times 10^{-4}$ mol based on the olefin), followed by heating to 70° C. After the internal temperature became stable, 15 g (0.12 mol) of trimethoxysilane was added dropwise to the flask over four hours at 70 to 80° C., and the reaction mixture was stirred at that temperature for two hours. By distillation of the reaction mixture thus obtained, 51 g of a colorless transparent fraction with a boiling point of 125 to 126° C./0.2 kPa was obtained.

Figure 3:
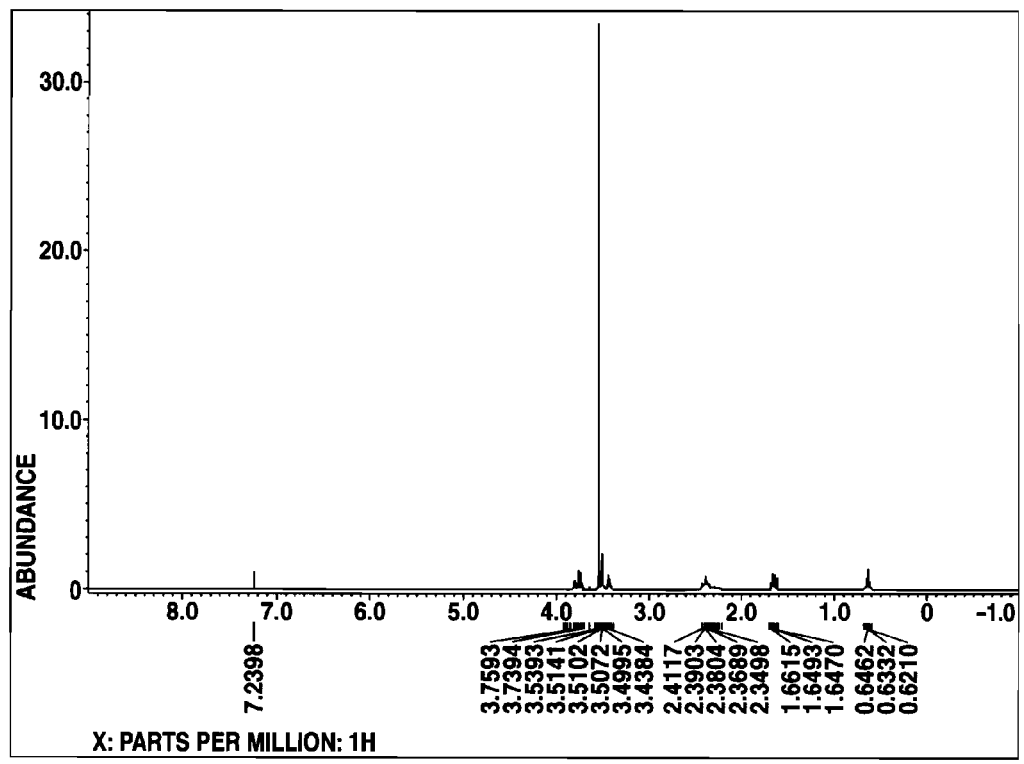
FIG. 3 shows $^1$H-NMR spectrum of an alkoxysilane compound obtained in Example 2.
Figure 4:
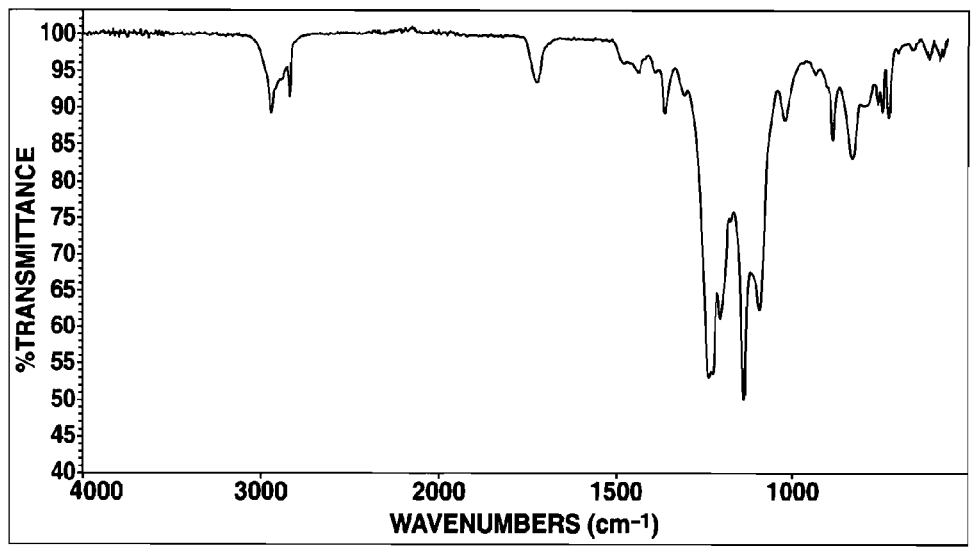
FIG. 4 shows IR spectrum of the alkoxysilane compound obtained in Example 2.

The fraction obtained was subjected to measurement of mass spectrum, $^1$H-NMR spectrum (heavy chloroform solvent), and IR spectrum, by a chemical ionization method using methane gas as a reaction gas. The result of mass spectrum is set forth below. FIG. 3 shows a $^1$H-NMR spectrum chart, and FIG. 4 an IR spectrum chart.

Mass spectrum: m/z 671, 523, 437, 393, 163, 121

Based on the above results, the compound obtained was identified as a compound of the following formula (12).

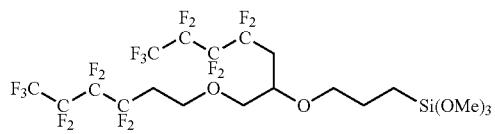

(12)

Example 3

A flask equipped with a stirrer, a reflux condenser, a dropping funnel and a thermometer was charged with 52 g (0.10 mol) of an olefin represented by the following formula (13),

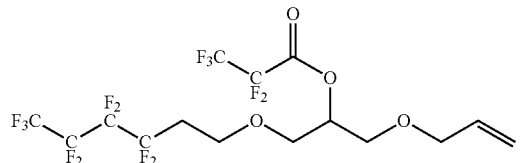

(13)

and a toluene solution of a platinum-1,3-divinyl-1,1,3,3-tetramethyldisiloxane complex ($1.0 \times 10^{-4}$ mol based on the olefin), followed by heating to 70° C. After the internal temperature became stable, 9.8 g (0.08 mol) of trimethoxysilane was added dropwise to the flask over four hours at 70 to 80° C., and the mixture in the flask was stirred for two hours at that temperature. By distillation of the resulting reaction mixture, 32 g of a colorless transparent fraction with a boiling point of 140 to 141° C./0.1 kPa was obtained.

Figure 5:
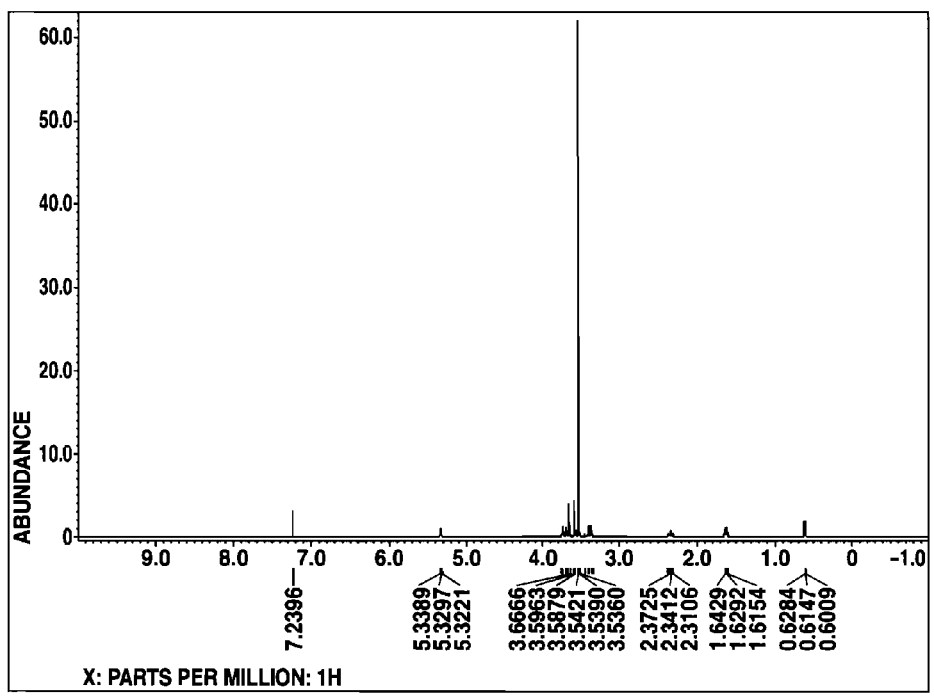
FIG. 5 shows $^1$H-NMR spectrum of an alkoxysilane compound obtained in Example 3.
Figure 6:
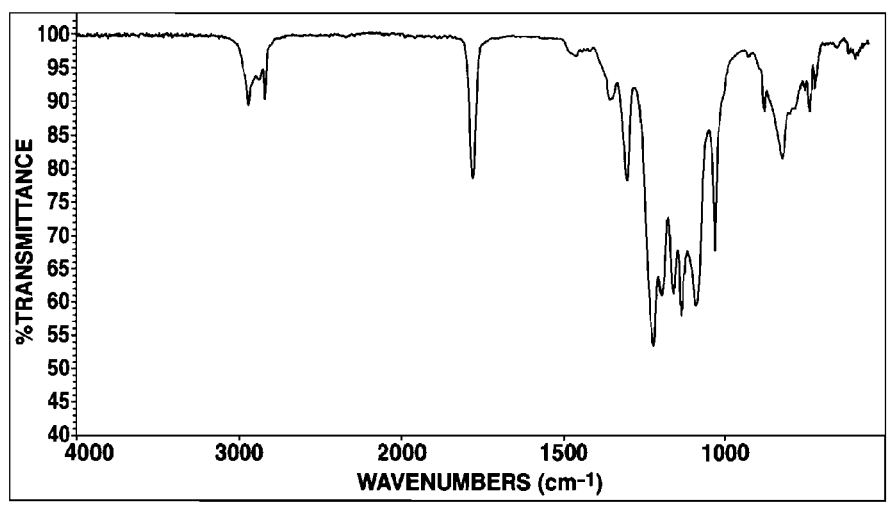
FIG. 6 shows IR spectrum of the alkoxysilane compound obtained in Example 3.

The fraction thus obtained was subjected to measurement of mass spectrum, $^1$H-NMR spectrum (heavy chloroform solvent), and IR spectrum, by a chemical ionization method using methane gas as a reaction gas. The result of mass spectrum is set forth below. In addition, FIG. 5 shows a $^1$H-NMR spectrum chart, and FIG. 6 shows an IR spectrum chart.

Mass spectrum: m/z 615, 467, 303, 163, 121

Based on the above results, the compound obtained was identified as a compound of the following formula (14).

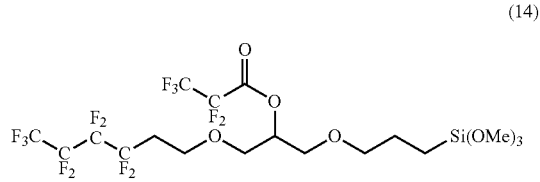

(14)

Example 4

A flask equipped with a stirrer, a reflux condenser, a dropping funnel and a thermometer was charged with 73 g (0.15 mol) of an olefin represented by the following formula (15),

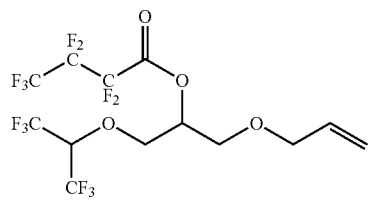

(15)

and a toluene solution of a platinum-1,3-divinyl-1,1,3,3-tetramethyldisiloxane complex ($1.0 \times 10^{-4}$ mol based on the olefin), followed by heating to 70° C. After the internal temperature became stable, 15 g (0.12 mol) of trimethoxysilane was added dropwise to the flask over four hours at 70 to 80° C., and the mixture in the flask was stirred at that temperature for two hours. By distillation of the resulting reaction mixture, 49 g of a colorless transparent fraction with a boiling point of 136 to 138° C./0.4 kPa was obtained.

Figure 7:
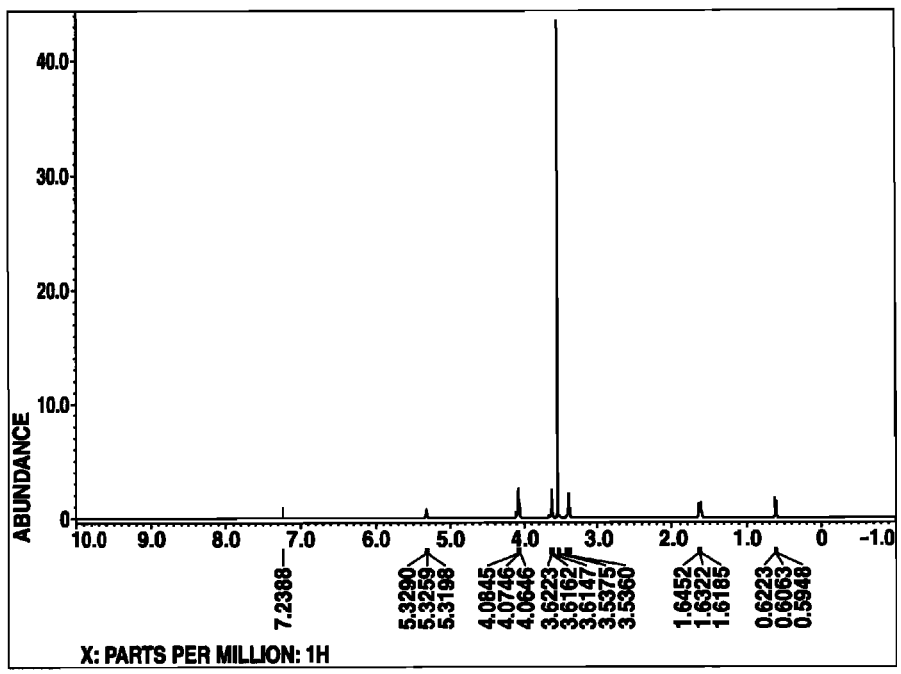
FIG. 7 shows $^1$H-NMR spectrum of an alkoxysilane compound obtained in Example 4.
Figure 8:
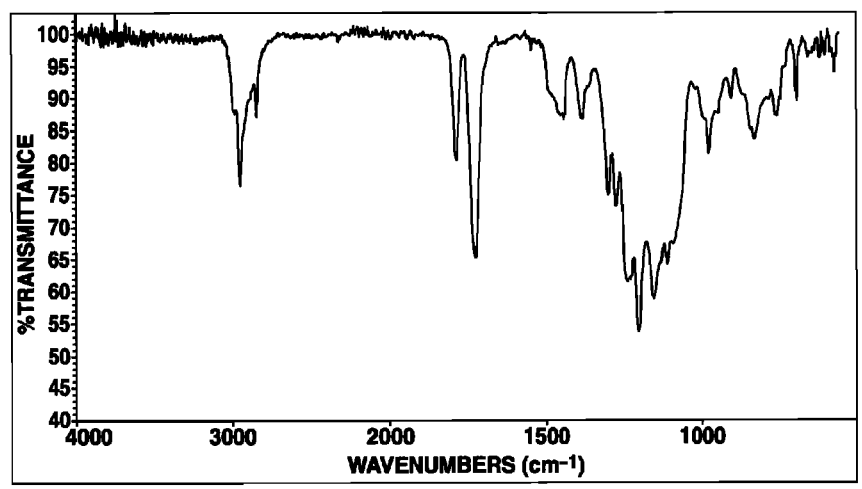
FIG. 8 shows IR spectrum of the alkoxysilane compound obtained in Example 4.

The fraction thus obtained was subjected to measurement of mass spectrum, $^1$H-NMR spectrum (heavy chloroform solvent), and IR spectrum, by a chemical ionization method using isobutane gas as a reaction gas. The result of mass spectrum is set forth below. FIG. 7 shows a $^1$H-NMR spectrum chart, and FIG. 8 an IR spectrum chart.

Mass spectrum: m/z 569, 421, 359, 163, 121

Based on the above results, the compound obtained was identified as a compound of the following formula (16).

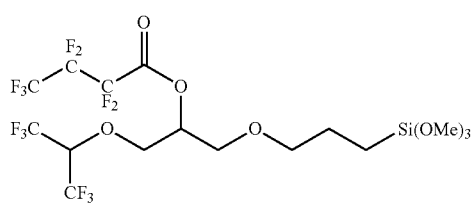

(16)

Example 5

A flask equipped with a stirrer, a reflux condenser, a dropping funnel and a thermometer was charged with 57 g (0.15 mol) of an olefin represented by the following formula (17),

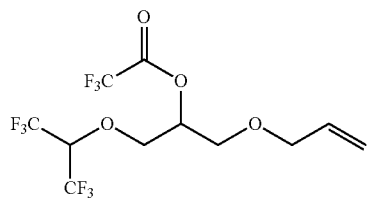

(17)

and a toluene solution of a platinum-1,3-divinyl-1,1,3,3-tetramethyldisiloxane complex ($1.0 \times 10^{-4}$ mol based on the olefin), followed by heating to 70° C. After the internal temperature became stable, 15 g (0.12 mol) of trimethoxysilane was added dropwise to the flask over four hours at 70 to 80° C., and the mixture in the flask was stirred at that temperature for two hours. By distillation of the resulting reaction mixture, 40 g of a colorless transparent fraction with a boiling point of 126 to 130° C./0.2 kPa was obtained.

Figure 9:
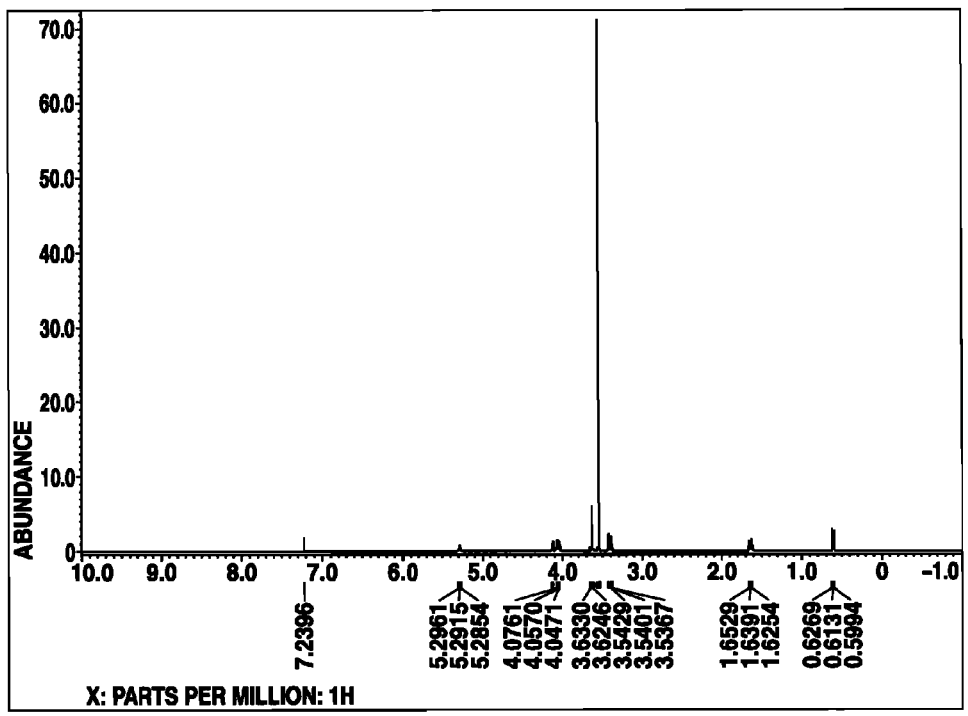
FIG. 9 shows $^1$H-NMR spectrum of an alkoxysilane compound obtained in Example 5.
Figure 10:
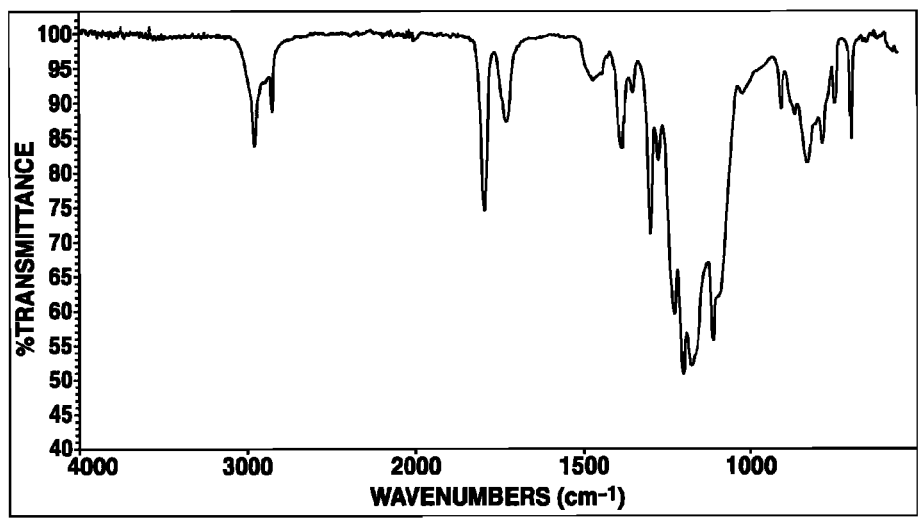
FIG. 10 shows IR spectrum of the alkoxysilane compound obtained in Example 5.

The fraction obtained was subjected to measurement of mass spectrum, $^1$H-NMR spectrum (heavy chloroform solvent) and IR spectrum, by a chemical ionization method using isobutane gas as a reaction gas. The result of mass spectrum is set forth below. FIG. 9 shows a $^1$H-NMR spectrum chart, and FIG. 10 an IR spectrum chart.

Mass spectrum: m/z 469, 321, 259, 163, 121

Based on the above results, the compound obtained was identified as a compound of the following formula (18).

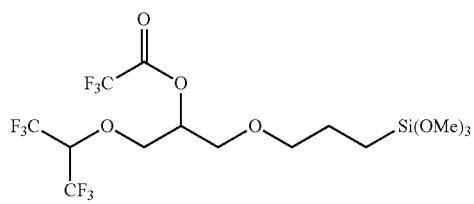

(18)

Example 6

A flask equipped with a stirrer, a reflux condenser, a dropping funnel and a thermometer was charged with 31 g (0.15 mol) of an olefin represented by the following formula (19),

(19)

and a toluene solution of a platinum-1,3-divinyl-1,1,3,3-tetramethyldisiloxane ($1.0 \times 10^{-4}$ mol based on the olefin), followed by heating to 70° C. After the internal temperature became stable, 19 g (0.14 mol) of trichlorosilane was added dropwise to the flask over four hours at 70 to 80° C., and the resulting reaction mixture was stirred at that temperature for two hours. It was confirmed that a compound of the following formula (20)

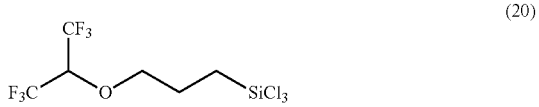

(20)

had been produced in the reaction mixture. After cooling to room temperature, the flask was charged with 47 g (0.46 mol) of triethylamine and 125 ml of toluene, then 15 g (0.46 mol) of methanol was added dropwise to the flask over two hours at 20 to 30° C., and the resulting mixture was stirred at that temperature for one hour. Thereafter, water was added to the reaction mixture, and, after the dissolution of the resulting triethylamine hydrochloride, liquid separation was conducted. The organic layer was distilled, to obtain 35 g of a colorless transparent fraction with a boiling point of 111 to 112° C./5.0 kPa.

Figure 11:
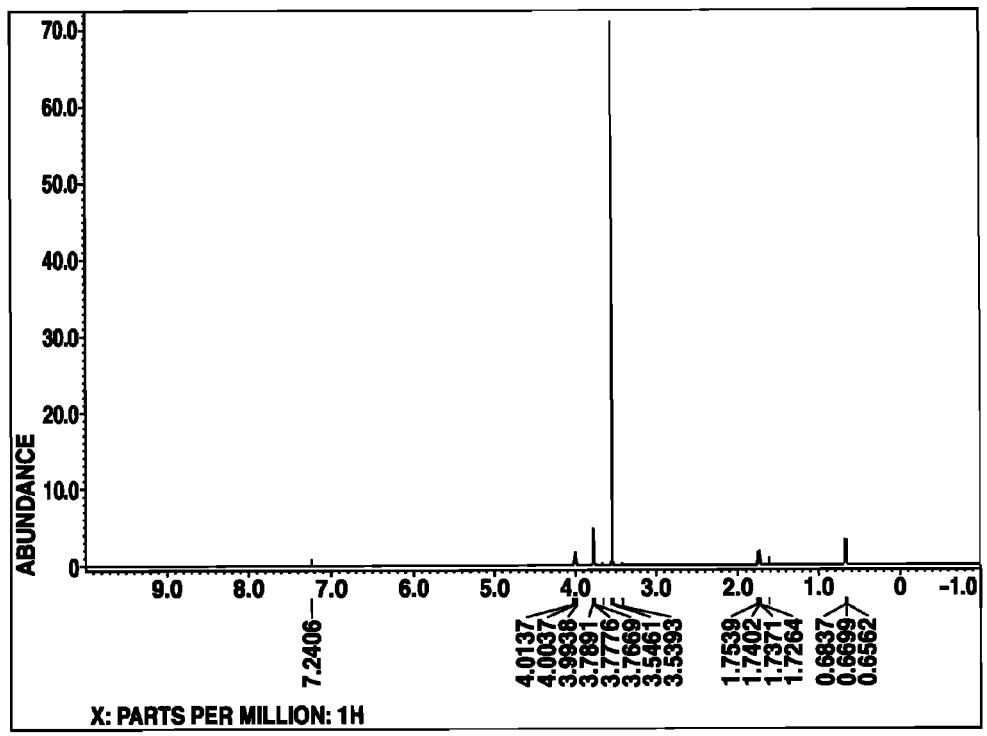
FIG. 11 shows $^1$H-NMR spectrum of an alkoxysilane compound obtained in Example 6.
Figure 12:
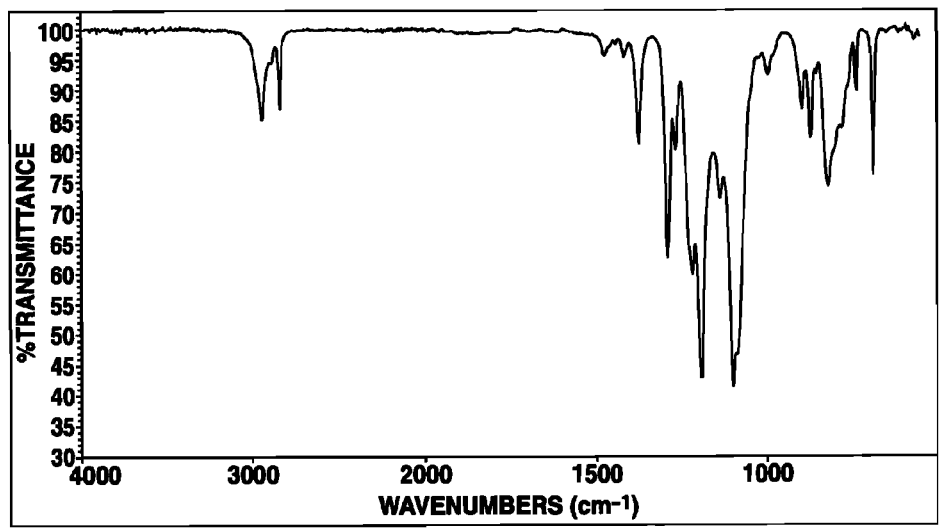
FIG. 12 shows IR spectrum of the alkoxysilane compound obtained in Example 6.

The fraction thus obtained was subjected to measurement of mass spectrum, $^1$H-NMR spectrum (heavy chloroform solvent) and IR spectrum, by a chemical ionization method using isobutane gas as a reaction gas. The result of mass spectrum is set forth below. FIG. 11 shows a $^1$H-NMR spectrum chart, and FIG. 12 an IR spectrum chart.

Mass spectrum: m/z 331, 299, 257, 163, 121

Based on the above results, the compound obtained was identified as a compound of the following formula (21).

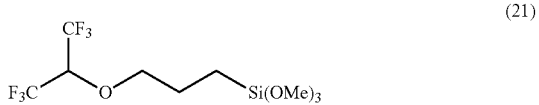

(21)

Example 7

A flask equipped with a stirrer, a reflux condenser, a dropping funnel and a thermometer was charged with 31 g (0.15 mol) of an olefin represented by the following formula (22),

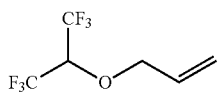
(22)

and a toluene solution of a platinum-1,3-divinyl-1,1,3,3-tetramethyldisiloxane ($1.0 \times 10^{-4}$ mol based on the olefin), followed by heating to 70° C. After the internal temperature became stable, 18.8 g (0.14 mol) of methyldiethoxysilane was added dropwise to the flask over four hours at 70 to 80° C., and the mixture in the flask was stirred at that temperature for two hours. By distillation of the resulting reaction mixture, 22 g of a colorless transparent fraction with a boiling point of 96 to 98° C./2.0 kPa was obtained.

Figure 13:
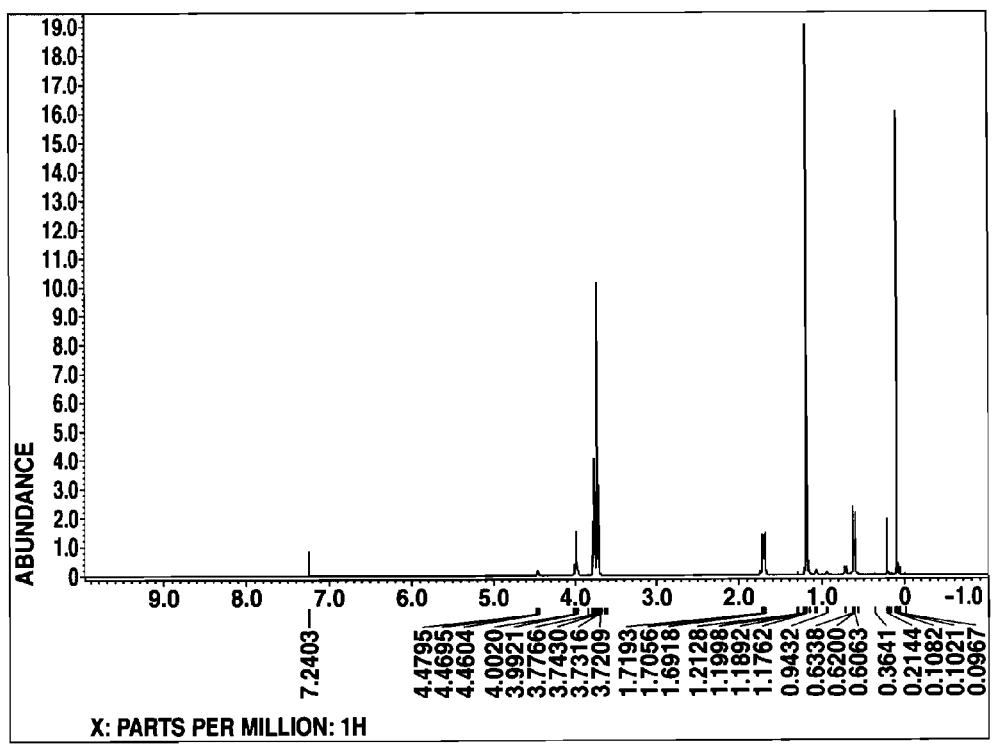
FIG. 13 shows $^1$H-NMR spectrum of an alkoxysilane compound obtained in Example 7.
Figure 14:
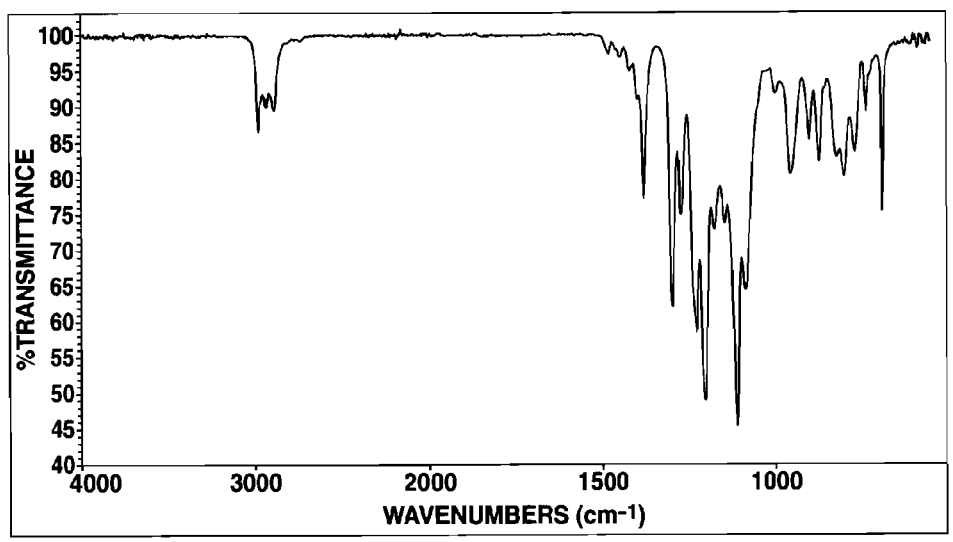
FIG. 14 shows IR spectrum of the alkoxysilane compound obtained in Example 7.

The fraction thus obtained was subjected to measurement of mass spectrum, $^1$H-NMR spectrum (heavy chloroform solvent) and IR spectrum, by a chemical ionization method using isobutane gas as a reaction gas. The result of mass spectrum is set forth below. FIG. 13 shows a $^1$H-NMR spectrum chart, and FIG. 14 an IR spectrum chart.

Mass spectrum: m/z 343, 297, 227, 207, 133

Based on the above results, the compound obtained was identified as a compound of the following formula (23).

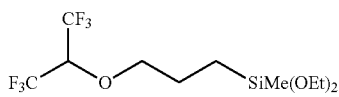
(23)

Comparative Examples as follows was added to a mixture of 13 g of a 0.2 wt % aqueous acetic acid solution and 44 g of ethanol, the resulting mixture was stirred for two hours. In the solution thus obtained, a glass plate was immersed for two hours, and the glass plate taken out from the solution was dried at 70° C. for two hours. Onto the glass plate thus surface-treated, water (1 μl) or tetradecane (5 μl) was dropped, and the contact angle was measured. Sliding angle was measured by a method in which water (13 μl) was dropped onto a glass plate, then the glass plate was tilted, and the tilting angle at which the water droplet started moving was measured. In addition, the difference (hysteresis) between the advancing contact angle and the receding contact angle was calculated. The results are shown in Table 3 below.

Incidentally, the fluoroalkylalkoxysilane compounds used in Comparative Examples 1 to 3 are the following compounds.

Comparative Example 1

8,8,8,7,7,6,6,5,5,4,4,3,3-tetradecafluorooctyltrimethoxysilane

Comparative Example 2

6,6,6,5,5,4,4,3,3-nonafluorohexyltrimethoxysilane

Comparative Example 3

3,3,3-trifluoropropyltrimethoxysilane

TABLE 3

| | Silane compound | Fluoroalkyl chain in one molecule | Contact angle (°) | | Sliding angle (°) | |
|---|---|---|---|---|---|---|
| | | | Water | Tetradecane | Water | Hysteresis |
| Example 8 | Compound of Example 1 | —$C_6F_{13}$, —$C_4F_9$ | 108 | 58 | 22 | 18 |
| Example 9 | Compound of Example 2 | —$C_4F_9 \times 2$ | 109 | 61 | 17 | 12 |
| Example 10 | Compound of Example 3 | —$C_4F_9$, —$C_2F_5$ | 104 | 56 | 21 | 12 |
| Example 11 | Compound of Example 4 | —$C_3F_6H$, —$C_3F_7$ | 102 | 53 | 23 | 15 |
| Example 12 | Compound of Example 5 | —$C_3F_6H$, —$CF_3$ | 90 | 47 | 12 | 8 |
| Example 13 | Compound of Example 6 | —$CF_3 \times 2$ | 87 | 48 | 18 | 10 |
| Comparative Example 1 | Compound of Comparative Example 1 | —$C_6F_{13}$ | 102 | 53 | 34 | 22 |
| Comparative Example 2 | Compound of Comparative Example 2 | —$C_4F_9$ | 96 | 50 | 44 | 23 |
| Comparative Example 3 | Compound of Comparative Example 3 | —$CF_3$ | 72 | 37 | 29 | 16 |

Examples 8 to 13 and Comparative Examples 1 to 3

Use as Glass Surface Treating Agent

After 0.1 mol of each of the alkoxysilane compounds having two fluoroalkyl groups synthesized in the above Examples or each of fluoroalkylalkoxysilane compounds of Japanese Patent Application No. 2011-087866 is incorporated herein by reference.

Although some preferred embodiments have been described, many modifications and variations may be made thereto in light of the above teachings. It is therefore to be understood that the invention may be practiced otherwise

The invention claimed is:

1. An alkoxysilane compound having two fluoroalkyl groups and represented by the following general formula (1):

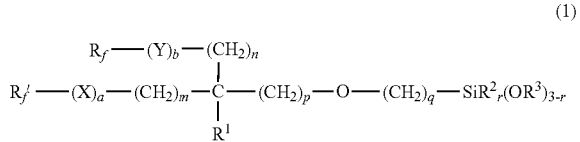

(1)

wherein $R_f$ and $R_f'$ are each independently a fluoroalkyl group of 1 to 10 carbon atoms, $R^1$ is a hydrogen atom or an aliphatic monovalent hydrocarbon group of 1 to 6 carbon atoms, $R^2$ and $R^3$ are each independently methyl group or ethyl group, X and Y are each independently an ether linkage or an ester linkage, a and b are each 0 or 1, m, n and p are each an integer of 0 to 6, q is an integer of 1 to 6, and r is an integer of 0 to 2.

2. The alkoxysilane compound having two fluoroalkyl groups according to claim 1 which is represented by the following general formula (2):

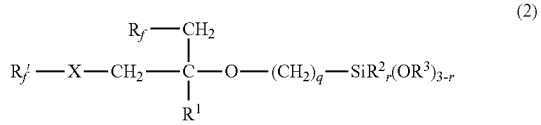

(2)

wherein $R_f$ and $R_f'$ are each independently a fluoroalkyl group of 1 to 10 carbon atoms, $R^1$ is a hydrogen atom or an aliphatic monovalent hydrocarbon group of 1 to 6 carbon atoms, $R^2$ and $R^3$ are each independently methyl group or ethyl group, X is an ether linkage or an ester linkage, q is an integer of 1 to 6, and r is an integer of 0 to 2.

3. The alkoxysilane compound having two fluoroalkyl groups according to claim 1 which is represented by the following general formula (3):

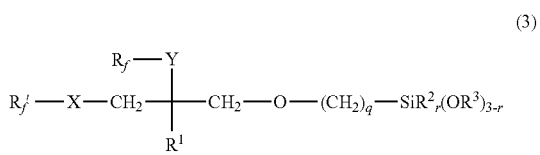

(3)

wherein $R_f$ and $R_f'$ are each independently a fluoroalkyl group of 1 to 10 carbon atoms, $R^1$ is a hydrogen atom or an aliphatic monovalent hydrocarbon group of 1 to 6 carbon atoms, $R^2$ and $R^3$ are each independently methyl group or ethyl group, X and Y are each independently an ether linkage or an ester linkage, q is an integer of 1 to 6, and r is an integer of 0 to 2.

4. The alkoxysilane compound having two fluoroalkyl groups according to claim 1 which is represented by the following formula (4):

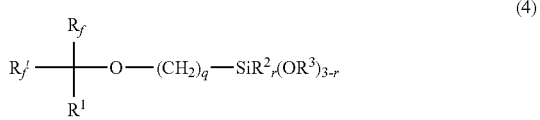

(4)

wherein $R_f$ and $R_f'$ are each independently a fluoroalkyl group of 1 to 10 carbon atoms, $R^1$ is a hydrogen atom or an aliphatic monovalent hydrocarbon group of 1 to 6 carbon atoms, $R^2$ and $R^3$ are each independently methyl group or ethyl group, q is an integer of 1 to 6, and r is an integer of 0 to 2.

* * * * *